(12) United States Patent
Anderson et al.

(10) Patent No.: US 9,839,706 B2
(45) Date of Patent: *Dec. 12, 2017

(54) INACTIVATION OF GRAM-POSITIVE BACTERIA

(71) Applicant: University of Strathclyde, Glasgow (GB)

(72) Inventors: John Galloway Anderson, East Kilbride (GB); Michelle Maclean, Glasgow (GB); Gerald Alexander Woolsey, Queensland (AU); Scott John MacGregor, Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/657,398

(22) Filed: Mar. 13, 2015

(65) Prior Publication Data

US 2015/0182646 A1 Jul. 2, 2015

Related U.S. Application Data

(63) Continuation of application No. 11/997,227, filed as application No. PCT/GB2006/002841 on Jul. 28, 2006, now Pat. No. 9,039,966.

(30) Foreign Application Priority Data

Jul. 29, 2005 (GB) .................................. 0515550.2

(51) Int. Cl.
*A61L 9/00* (2006.01)
*A62B 7/08* (2006.01)
(Continued)

(52) U.S. Cl.
CPC ................ *A61L 2/084* (2013.01); *A61L 9/18* (2013.01); *A61N 5/06* (2013.01); *A61L 2/0052* (2013.01)

(58) Field of Classification Search
CPC ................................. A61L 2/084; A61N 5/06
See application file for complete search history.

(56) References Cited

U.S. PATENT DOCUMENTS

| | | |
|---|---|---|
| 3,926,556 A | 12/1975 | Boucher |
| 4,910,942 A | 3/1990 | Dunn et al. |

(Continued)

FOREIGN PATENT DOCUMENTS

| | | |
|---|---|---|
| AU | 2006273860 B2 | 4/2012 |
| CA | 2617205 A1 | 2/2007 |

(Continued)

OTHER PUBLICATIONS

Ashkenazi, H., et al., "Eradication of Propionibacterium Acnes by its Endogenic Porphyrins after Illumination with High Intensity Blue Light", FEMS Immunology and Medical Microbiology, Jan. 2003, pp. 17-24, vol. 35, Elsevier Science B.V., The Netherlands.

(Continued)

*Primary Examiner* — Kevin Joyner
(74) *Attorney, Agent, or Firm* — Alston & Bird LLP

(57) ABSTRACT

A method for inactivating medically important Gram-positive bacteria including Methicillin-resistant *Staphylococcus aureus* (MRSA), Coagulase-Negative *Staphylococcus* (CONS), *Streptococcus*, *Enterococcus* and *Clostridium* species, comprising exposure to visible light, and in particular light within the wavelength range 400-500 nm.

4 Claims, 16 Drawing Sheets

(51) Int. Cl.
 A61L 2/08 (2006.01)
 A61N 5/06 (2006.01)
 A61L 9/18 (2006.01)
 A61L 2/00 (2006.01)

(56) References Cited

U.S. PATENT DOCUMENTS

| | | |
|---|---|---|
| 6,251,127 B1 | 6/2001 | Biel |
| 6,627,730 B1 | 9/2003 | Burnie |
| 9,039,966 B2 | 5/2015 | Anderson et al. |
| 2003/0023284 A1 | 1/2003 | Gartstein et al. |
| 2004/0147986 A1 | 7/2004 | Baumgardner et al. |
| 2005/0049228 A1 | 3/2005 | Albrecht et al. |
| 2005/0055070 A1 | 3/2005 | Jones et al. |
| 2005/0104059 A1 | 5/2005 | Friedman et al. |
| 2005/0107849 A1 | 5/2005 | Altshuler et al. |
| 2005/0107853 A1 | 5/2005 | Krespi et al. |
| 2006/0085052 A1 | 4/2006 | Feuerstein et al. |
| 2009/0076115 A1 | 3/2009 | Wharton et al. |

FOREIGN PATENT DOCUMENTS

| | | |
|---|---|---|
| CN | 101272822 B | 12/2012 |
| EP | 0306301 A1 | 3/1989 |
| EP | 1 495 820 A1 | 1/2005 |
| EP | 1924323 A1 | 5/2008 |
| EP | 1493820 B1 | 5/2013 |
| FR | 2 773 715 A1 | 7/1999 |
| GB | 2442705 B | 11/2009 |
| JP | 10-156349 A | 6/1998 |
| JP | 2004-261595 A | 9/2004 |
| JP | 2004-262595 A | 9/2004 |
| JP | 2004-275335 A | 10/2004 |
| JP | 2004-275927 A | 10/2004 |
| JP | 2007-511279 A | 5/2007 |
| JP | 05689580 B2 | 3/2015 |
| KR | 10-195941 B1 | 6/1999 |
| KR | 20-0357464 | 7/2004 |
| KR | 20-0371914 | 12/2004 |
| KR | 2008-052561 A | 6/2008 |
| KR | 2013-136597 A | 12/2013 |
| WO | WO 03/037504 A1 | 5/2003 |
| WO | WO 03/084601 | 10/2003 |
| WO | WO 03/089063 | 10/2003 |
| WO | WO 05/048811 | 6/2005 |
| WO | WO 2005/049138 A1 | 6/2005 |
| WO | WO 2007/012875 A1 | 2/2007 |

OTHER PUBLICATIONS

Australian Government, IP Australia, Examiner's First Report for Application No. 2006273860, dated Jul. 16, 2010, 2 pages, Australia.
Australian Government, IP Australia, Examiner's Second Report for Application No. 2006273860, dated Oct. 19, 2011, 3 pages, Australia.
Australian Government, IP Australia, Notice of Acceptance for Application No. 2006273860, dated Apr. 10, 2012, 3 pages, Australia.
Bek-Thomsen, M., et al., "Acne is Not Associated with Yet-Uncultured Bacteria", J. Clin. Microbiol., Oct. 2008, pp. 3355-3360, vol. 46, No. 10, American Society for Microbiology, U.S.A.
Canadian Intellectual Property Office, Requisition by the Examiner for Application No. 2,617,205, dated Feb. 1, 2013, 3 pages, Canada.
Canadian Intellectual Property Office, Requisition by the Examiner for Application No. 2,617,205, dated Jan. 10, 2014, 3 pages, Canada.
Canadian Intellectual Property Office, Requisition by the Examiner for Application No. 2,617,205, dated Feb. 20, 2015, 4 pages, Canada.
European Patent Office, Brief Communication, Oral Proceedings on Mar. 1, 2016, for Application No. 06765156.2, dated Feb. 22, 2016, 5 pages, Germany.
European Patent Office, Communication pursuant to Article 94(3) EPC for Application No. 06765156.2, dated Aug. 4, 2010, 3 pages, Germany.
European Patent Office, Communication pursuant to Article 94(3) EPC for Application No. 06765156.2, dated Sep. 20, 2012, 4 pages, Germany.
European Patent Office, Communication pursuant to Article 94(3) EPC for Application No. 06765156.2, dated Feb. 3, 2014, 5 pages, Germany.
European Patent Office, Communication under Rule 71(3) EPC, Intention to Grant for Application No. 06765156.2, dated Mar. 21, 2016, 36 pages, Germany.
International Searching Authority, *Corrected* International Search Report for Application No. PCT/GB2006/002841, dated Feb. 28, 2007, 5 pages, The Netherlands.
International Searching Authority, International Search Report and Written Opinion for International Application No. PCT/GB2006/002841, dated Nov. 17, 2006, 9 pages, The Netherlands.
Japan Patent Office, Decision of Refusal for Application No. 2008-523460, drafted May 14, 2014, 10 pages, Japan.
Japan Patent Office, Decision to Grant a Patent Application No. 2008-523460, drafted Jan. 6, 2015, 6 pages, Japan.
Japan Patent Office, Notification of Reasons for Refusal for Application No. 2008-523460, drafted Aug. 13, 2013, 4 pages, Japan.
Japan Patent Office, Notification of Reasons for Refusal for Application No. 2008-523460, drafted Jul. 13, 2012, 6 pages, Japan.
Kawada, Akira, et al., "Acne phototherapy with a high-intensity, enhanced, narrow-band, blue light source: an open study and in vitro investigation", Journal of Dermatological Science, Nov. 2002, pp. 129-135, vol. 30, No. 2, Elsevier Science Ireland Ltd., Ireland.
Korean Intellectual Property Office, Notification of Final Rejection for Application No. 10-2008-7003589, dated Aug. 5, 2013, 4 pages, Republic for Korea.
Korean Intellectual Property Office, Notification of Final Rejection 10-2013-7032244, dated Aug. 20, 2014, 2 pages, Republic of Korea.
Korean Intellectual Property Office, Notification of Reason for Refusal for Application No. 10-2008-7003589, dated Oct. 16, 2012, 5 pages, Republic for Korea.
Korean Intellectual Property Office, Decision of Rejection for Amendment for Application No. 10-2008-7003589, dated Jan. 15, 2014, 4 pages, Republic for Korea.
Korean Intellectual Property Office, Notification of Reason for Refusal 10-2013-7032244, dated Dec. 24, 2013, 5 pages, Republic of Korea.
Korean Intellectual Property Office, Notification of Result of Reexamination 10-2008-7003589, dated Jan. 15, 2014, 2 pages, Republic of Korea.
The International Bureau of WIPO, International Preliminary Report on Patentability for International Application No. PCT/GB2006/002841, dated Jan. 29, 2008, 7 pages, Switzerland.
UK Intellectual Property Office, Examination under Section 18(3) for Application No. 0617960.0, dated May 1, 2007, 2 pages, U.K.
UK Intellectual Property Office, Examination under Section 18(3) for Application No. 0617960.0, dated Feb. 14, 2008, 1 page, U.K.
UK Intellectual Property Office, Notification of Grant for Application No. 0617960.0, dated Oct. 13, 2009, 3 pages, U.K.
United States Patent and Trademark Office, Notice of Allowance and Fee(s) Due for U.S. Appl. No. 11/997,227, dated Feb. 12, 2015, 11 pages, U.S.A.
United States Patent and Trademark Office, Notice of Allowance and Fee(s) Due for U.S. Appl. No. 11/997,227, dated Mar. 2, 2015, 10 pages, U.S.A.
United States Patent and Trademark Office, Office Action for U.S. Appl. No. 11/997,227, dated Nov. 25, 2008, 7 pages, U.S.A.
United States Patent and Trademark Office, Office Action for U.S. Appl. No. 11/997,227, dated Sep. 14, 2009, 7 pages, U.S.A.
United States Patent and Trademark Office, Office Action for U.S. Appl. No. 11/997,227, dated Jan. 28, 2010, 7 pages, U.S.A.
United States Patent and Trademark Office, Office Action for U.S. Appl. No. 11/997,227, dated Jul. 19, 2010, 9 pages, U.S.A.
United States Patent and Trademark Office, Office Action for U.S. Appl. No. 11/997,227, dated Mar. 7, 2011, 10 pages, U.S.A.

(56) References Cited

OTHER PUBLICATIONS

United States Patent and Trademark Office, Office Action for U.S. Appl. No. 11/997,227, dated Aug. 25, 2011, 8 pages, U.S.A.
United States Patent and Trademark Office, Office Action for U.S. Appl. No. 11/997,227, dated Sep. 12, 2012, 7 pages, U.S.A.
United States Patent and Trademark Office, Office Action for U.S. Appl. No. 11/997,227, dated Jun. 20, 2013, 10 pages, U.S.A.
United States Patent and Trademark Office, Office Action for U.S. Appl. No. 11/997,227, dated Dec. 4, 2013, 15 pages, U.S.A.
United States Patent and Trademark Office, Office Action for U.S. Appl. No. 11/997,227, dated Apr. 25, 2014, 11 pages, U.S.A.
Burkhart, C. N. and Gottwald, L., "Assessment of etiologic agents in acne pathogenesis," *Skinned*, 2003, vol. 2, No. 4, pp. 222-228.
Burkhart, C.G., et al., "Acne: a review of immunologic and microbiologic factors," *Postgraduate Medical Journal*, 1999, vol. 75, pp. 328-331.
Clauditz, A., et al., "Staphyloxanthin plays a role in the fitness of *Staphylococcus aureus* and its ability to cope with oxidative stress," *Infection and Immunity*, 2006, vol. 74, No. 8, pp. 4950-4953.
Harrison, A.P., "Survival of Bacteria," *Annu. Rev. Microbiol.*, 1967, pp. 143-156, vol. 21.
Jappe, U., "Pathological mechanisms of acne with special emphasis on *Proptonibacterium acnes* and related therapy," *Acta Dermato-Venereologica*, 2003, vol. 83, pp. 241-248.
Marshall, J.H. and Wilmoth, G.J., "Pigments of *Staphylococcus aureus*, a series of trierpenoid carotenoids," *J. Bacteriology*, 1981, vol. 147, No. 3, pp. 900-913.
Osnat Feuerstein, Nir Persman and Ervin I. Weiss, Phototoxic Effect of Visible Light on Porphyromonas gingivalis and Fusobacterium nucleatum: An In Vitro Study, Photochemistry and Photobiology, 2004, 80: 412-415, Dept. of Prosthodontics, Hebrew University-Hadassah School of Dental Medicine, Jerusalem, Israel.
Pelz, A. et al., "Structure and biosynthesis of staphyloxanthin from *Staphylococcus aureus*," *J.Bio. Chem.*, 2005, vol. 280, No. 37, pp. 32493-32498.
Pochi, P.E., "Acne: Androgens and microbiology," *Drug Dev. Res.*, 1988, vol. 13, pp. 157-168.
Sakai, K., et al., "Search for inhibitors of staphyloxanthin production by methicillin-resistant *Staphylcoccus aureus*," *Biol. Pharm. Bull*, 2012, vol. 35, No. 1, pp. 48-53.
Tong, Y. and Lighthart, B., "Solar radiation is shown to select for pigmented bacteria in the ambient outdoor atmosphere," *Photochemistry and Photobiology*, 1997, vol. 65, No. 1, pp. 103-106.
Tong, Y., et al., "Population study of atmospheric bacteria at the Fengtai district of Beijing on two representative days," *Aerobiologia*, 1993, vol. 9, pp. 69-74.

INACTIVATION OF GRAM-POSITIVE BACTERIA

CROSS-REFERENCE TO RELATED APPLICATIONS

This application is a Continuation of U.S. application Ser. No. 11/997,227, filed Jul. 3, 2008, which is a U.S. National Stage of International Application No. PCT/GB2006/002841, filed Jul. 28, 2006, which claims the benefit of Great Britain Application No. 0515550.2, filed Jul. 29, 2005, the contents of which are hereby incorporated herein in their entirety by reference.

The present invention relates to a method for inactivating medically important Gram-positive bacteria including *Staphylococcus aureus* and methicillin (multi)-resistant *Staphylococcus aureus* (MRSA), Coagulase-Negative *Staphylococcus* (CONS), *Streptococcus, Enterococcus* and *Clostridium* species.

BACKGROUND OF THE INVENTION

Methicillin-resistant *Staphylococcus aureus* (MRSA) is becoming an increasingly problematic micro-organism, with infection rates rising and effective methods of control becoming more and more limited. In addition to the resistance of MRSA to antibiotics, there is a significant problem due to the availability of few effective sterilisation methods for environmental decontamination; for example in air and on contact surfaces. Public and media interest in the transmission and control of MRSA is escalating and it is becoming one of the most significant problems within the healthcare industry. Hospitals and nursing homes are the worst affected areas. Furthermore, community-acquired MRSA is also now being recognised as an increasing problem, with transmission occurring in public and social areas such as public gyms and sports centres.

As well as MRSA, other Gram-positive bacteria are known to cause health problems, particularly in the hospital environment. For example, *Staphylococcus epidermidis*, which is a Coagulase-Negative *Staphylococcus* (CONS), can cause infection, particularly in infants and in hospitalised patients who have received prosthetic implant surgery. *Streptococcus pyogenes* is a Gram-positive coccus commonly associated with infections such as pharyngitis, pyoderma, scarlet fever, erysipelas, cellulitis, streptococcal toxic-shock syndrome, rheumatic fever, glomerulonephritis, bacteraemia and necrotizing fasciitis, often referred to as "flesh-eating bacteria". *Enterococcus faecalis* (another Gram-positive coccus) is a common cause of urinary tract and wound infections, as well as other infections including bacteraemia, endocarditis and meningitis in severely ill hospitalised patients. Multi-antibiotic resistance is also becoming a well-documented problem with enterococcal infections. *Clostridium* species, in particular *C. difficile*, have been associated with high mortality in elderly patients due to diarrohea-associated dehydration, medically known as antibiotic-associated pseudomembranous colitis.

Many techniques have been proposed for destroying harmful bacteria, such as MRSA. For example, U.S. Pat. No. 6,251,127 describes a photodynamic process for the inactivation of bacteria and fungal wound infections using methylene blue or toluidene blue. Light energy in combination with photosensitising agents is used to treat or detect pathologies of living tissue, including cancer and microbiological pathogens. The light used has wavelengths ranging from about 450 nm to about 850 nm. Tests demonstrate the efficacy of the light treatment in combination with the photosensitising agents for the destruction of *Staphylococcus aureus* in in-vivo infected wounds; and for in-vitro destruction of antibiotic-resistant *Staphylococcus, Streptococcus, Enterococcus, E. coli, Pseudomonas, Haemophilus influenza* and *Candida albicans*. In addition, wavelength spectra of activation of methylene blue and toluidene blue in the presence of various concentrations of the above bacteria and *Candida* have been provided.

Whilst in some environments, the methodology of U.S. Pat. No. 6,251,127 may be useful, it nevertheless suffers from the significant practical disadvantage that photosensitising agents must be applied to the bacteria that are to be inactivated. A similar problem arises with US2005/0049228, which also requires the combined use of a photosensitiser and light; in this case, in the range of 500 nm to 580 nm. The need for photosensitising agents is a significant limitation of these techniques.

An objective of the present invention is to provide a simple and effective technique for inactivating selected bacteria, in particular MRSA, and more generally the *Staphylococcus, Streptococcus, Enterococcus* and *Clostridium* species.

SUMMARY OF THE INVENTION

A method for inactivating one or more pathogenic gram-positive bacterial comprising exposure of the bacteria to visible light without using a photosensitiser.

Preferably said bacteria are selected from *Staphylococcus*, in particular MRSA, CONS, *Streptococcus, Enterococcus* and *Clostridium* species.

It is understood that the term pathogenic is used in the context of gram-positive bacterial species and/or strains, which are capable of causing disease or infection in a human or animal subject. It is also understood that some bacteria are often commensal in that they are able to colonise and/or live on/within a healthy host and not become pathogenic unless or until the host becomes immunocompromised and/or unhealthy due to some other form of disease or injury, such as a wound. Such "potentially" pathogenic bacteria are encompassed by the invention also.

Moreover, the term inactivation is understood to mean that said bacteria are killed, or damaged so as to reduce or inhibit bacterial replication. The methods and systems taught herein can therefore be considered as bactericidal and/or bacteriostatic and this may depend on the species/strain of bacteria, wavelength of light, dose, etc.

Exposing these bacteria to blue light, or white light containing blue light, has been found to stimulate an inactivation process. An advantage of using light in the visible-wavelength region is that there is no detrimental effect on human or animal health. Consequently, the method can be used for an extensive range of applications, such as air disinfection, contact-surface and materials disinfection and, most noteworthy, wound protection and tissue disinfection.

According to another aspect of the invention, there is provided a method for inactivating pathogenic gram positive bacteria including at least one of Methicillin-resistant *Staphylococcus aureus* (MRSA), Coagulase-Negative *Staphylococcus* (CONS), *Streptococcus, Enterococcus* and *Clostridium* species comprising exposure of the bacteria to visible light having a wavelength in the range 400-500 nm. The visible light may have a wavelength in the range 400-450 nm. The light may have a wavelength in the range 400-420 nm. The light may have a wavelength of 405 nm.

According to yet another aspect of the invention, there is provided a system for inactivating pathogenic Gram-positive bacteria including Methicillin-resistant *Staphylococcus aureus* (MRSA), Coagulase-Negative *Staphylococcus* (CONS), *Streptococcus, Enterococcus* and *Clostridium* species, comprising the means for exposing them to visible light having a wavelength in the range of 400-500 nm. The wavelength of the light used is preferably in the range 400-500 nm. The wavelength may be in the range 400-450 nm, and more specifically in the range 400-420 nm, with optimal inactivation at 405 nm.

According to still another aspect of the invention, there is provided use of visible light having a wavelength in the range of 400-500 nm, especially 400-420 nm for inactivating pathogenic gram positive bacteria including at least one of Methicillin-resistant *Staphylococcus aureus* (MRSA), Coagulase-Negative *Staphylococcus* (CONS), *Streptococcus, Enterococcus* and *Clostridium* species.

BRIEF DESCRIPTION OF THE DRAWINGS

Various aspects of the present invention will now be described by way of example only and with reference to the accompanying drawings, of which.

DETAILED DESCRIPTION OF THE DRAWINGS

Figure 1:
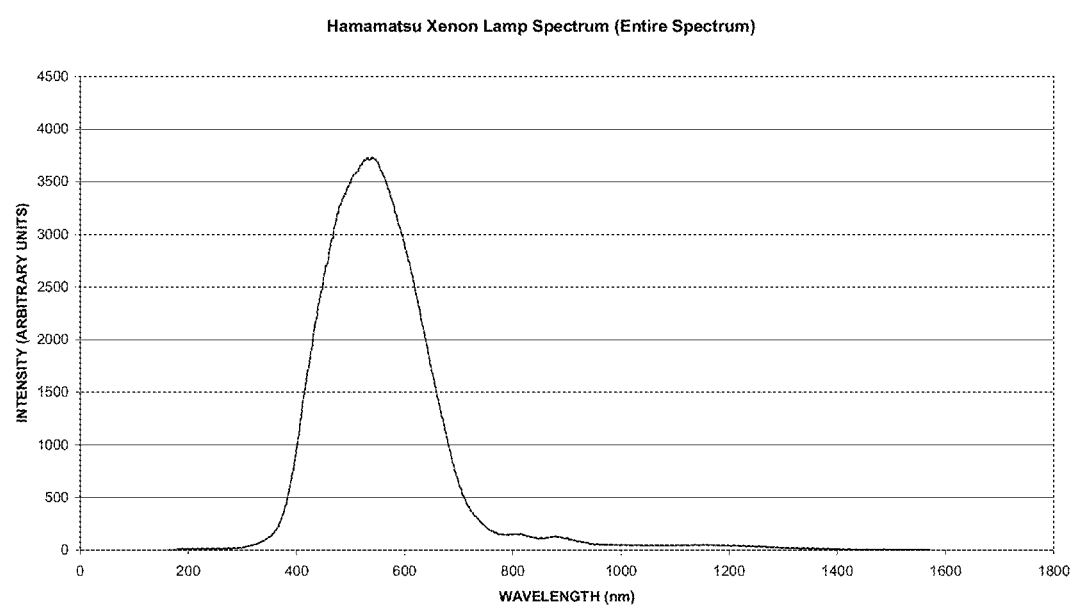
FIG. 1 shows the total emission spectrum of a Hamamatsu Xenon lamp.
Figure 2:
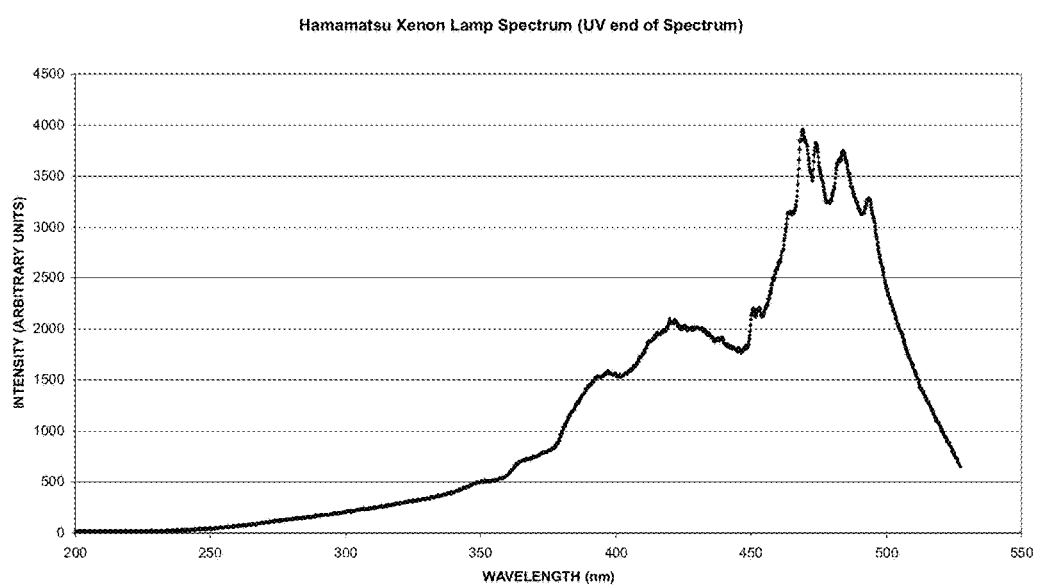
FIG. 2 shows in greater detail the ultra-violet emission spectrum of the Xenon lamp of FIG. 1.

Exposing MRSA to blue light has been found to cause significant inactivation. This narrow range of wavelength is part of the white-light spectrum. For all white-light sources, only a small fraction of the light output is in this range, typically one or two percent. Hence, to provide a sufficient amount of light and demonstrate the effectiveness of this technique, the source used was a Xenon lamp (Hamamatsu Photonics UK Limited). Emission spectra of the lamp are shown in FIGS. 1 and 2. The lamp was used in combination with an optical-fibre light guide and a selection of optical filters in order to allow exposure of the *Staphylococcus aureus* suspensions to specified wavelengths of visible light. The output of the light guide was maintained at a distance of 5 cm from the sample during all experiments.

To demonstrate the effectiveness of the technique, various studies have been carried out. The bacteria used were as follows: *Staphylococcus aureus* NCTC 4135; methicillin-resistant *Staphylococcus aureus* LMG 15975; methicillin-resistant *Staphylococcus aureus* 16a (clinical isolate), *Staphylococcus epidermidis* NCTC 7944, *Streptococcus pyogenes* NCTC 8198 *Enterococcus faecali* and *Clostridium perfringens* 13124. Each sample was serially diluted to the appropriate concentration using phosphate-buffered saline (PBS), plated out using nutrient agar (NA) and then incubated at 37° C. for 24 hours.

Figure 3:
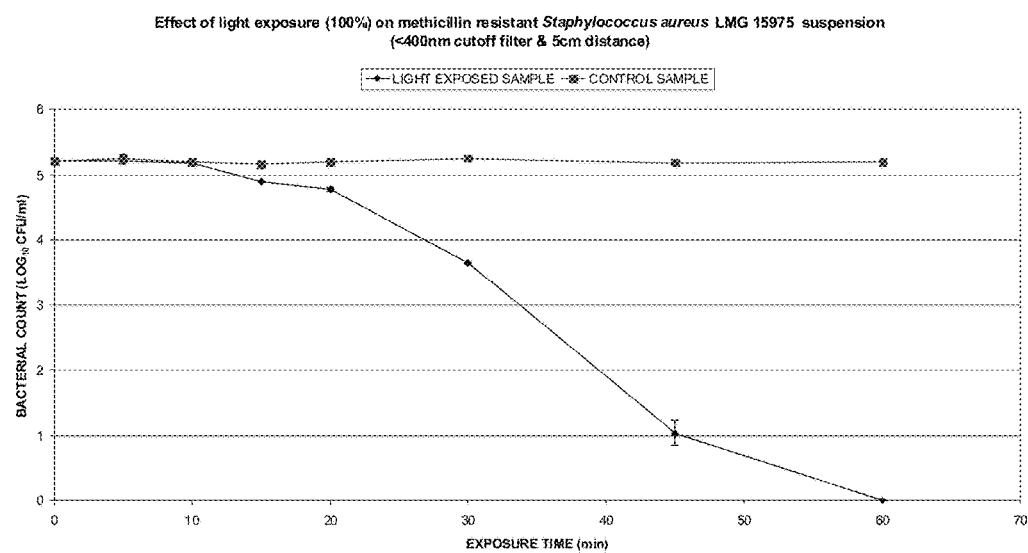
FIG. 3 is a plot of bacterial count of a methicillin-resistant *S. aureus* strain as a function of time of exposure to light of wavelength greater than 400 nm.
Figure 4:
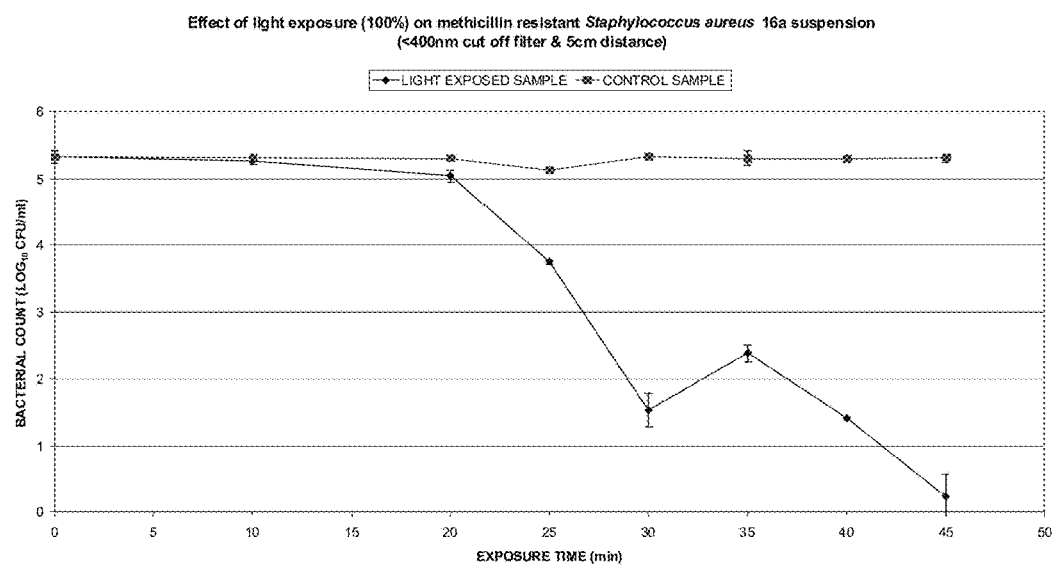
FIG. 4 is a plot of bacterial count of a second methicillin-resistant *S. aureus* strain as a function of time of exposure to light of wavelength greater than 400 nm.

Suspensions of methicillin-resistant *Staphylococcus aureus* LMG 15975 and clinical isolate 16a were prepared and exposed to visible light. The light was transmitted through a 400 nm long-wave pass filter (50% cut-off in transmission at 400 nm) before impacting on the bacterial suspension. This allowed only wavelengths of 400 nm and above (visible light) to illuminate the sample. The results of these experiments are shown in FIGS. 3 and 4. From these, it can be seen that the light treatment causes significant reduction in the counts of both the culture collection MRSA (LMG 15975) and the highly resistant clinical isolate (16a). The control data refer to samples that were untreated over the same time interval.

Figure 5:
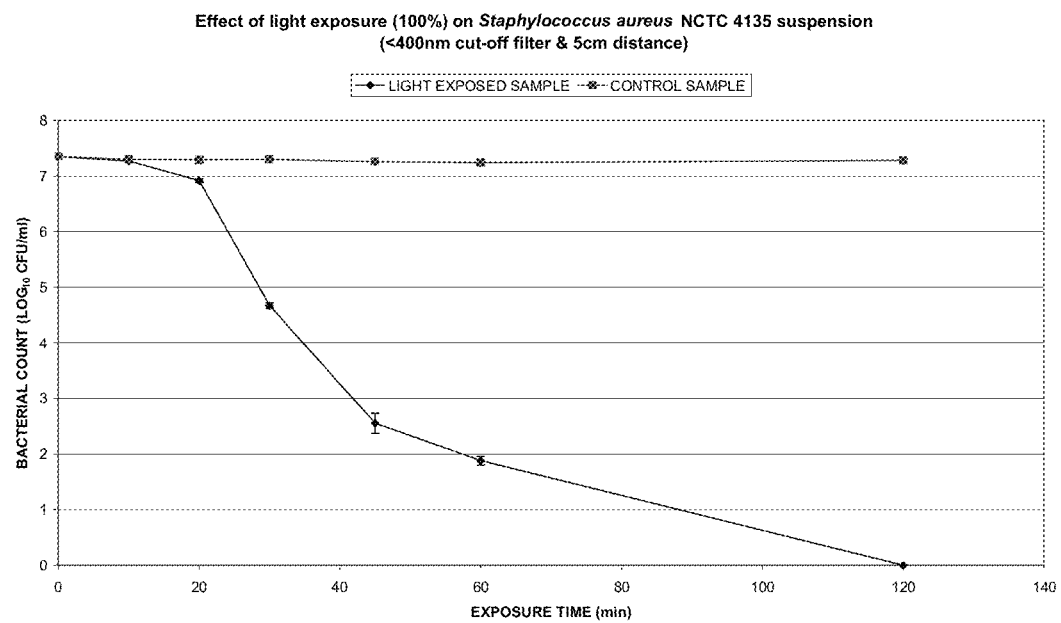
FIG. 5 is a plot of bacterial count of *S. aureus* NCTC 4135 as a function of time of exposure to light of wavelength greater than 400 nm.
Figure 6:
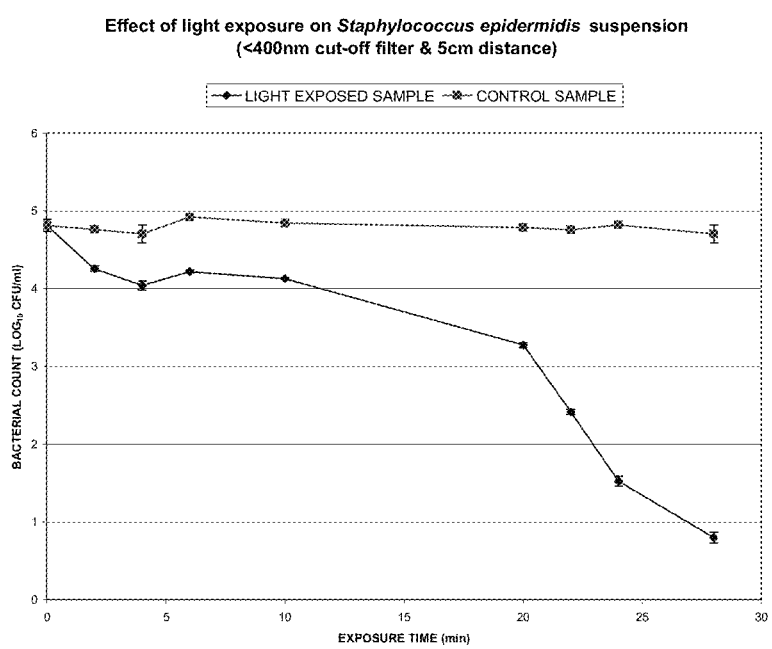
FIG. 6 is a plot of bacterial count of *S. epidermidis* NCTC 7944 as a function of time of exposure to light of wavelength greater than 400 nm.
Figure 7:
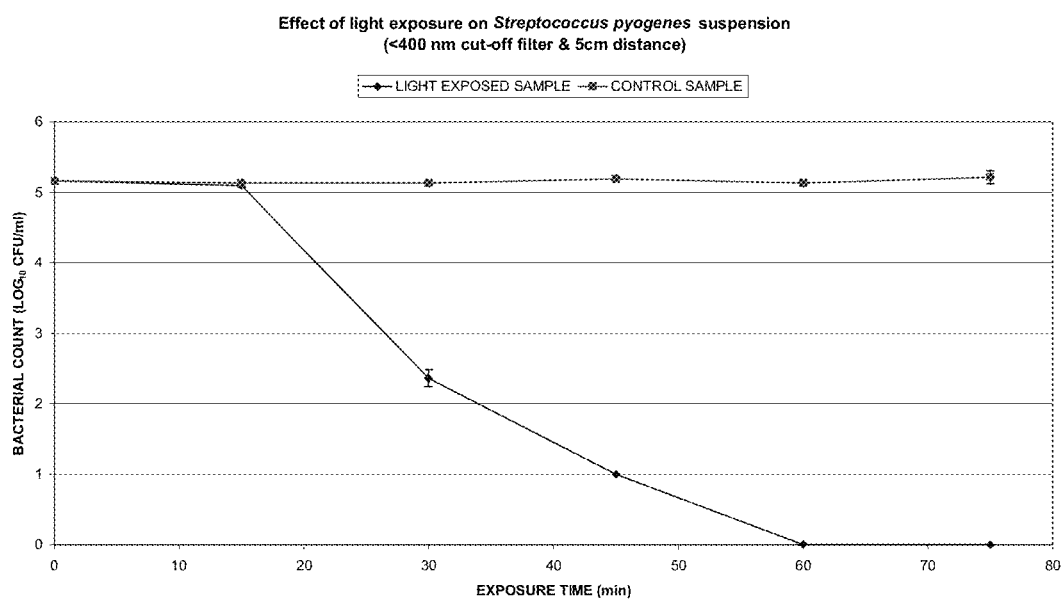
FIG. 7 is a plot of bacterial count of *Streptococcus pyogenes* NCTC 8198 as a function of time of exposure to light of wavelength greater than 400 nm.
Figure 8:
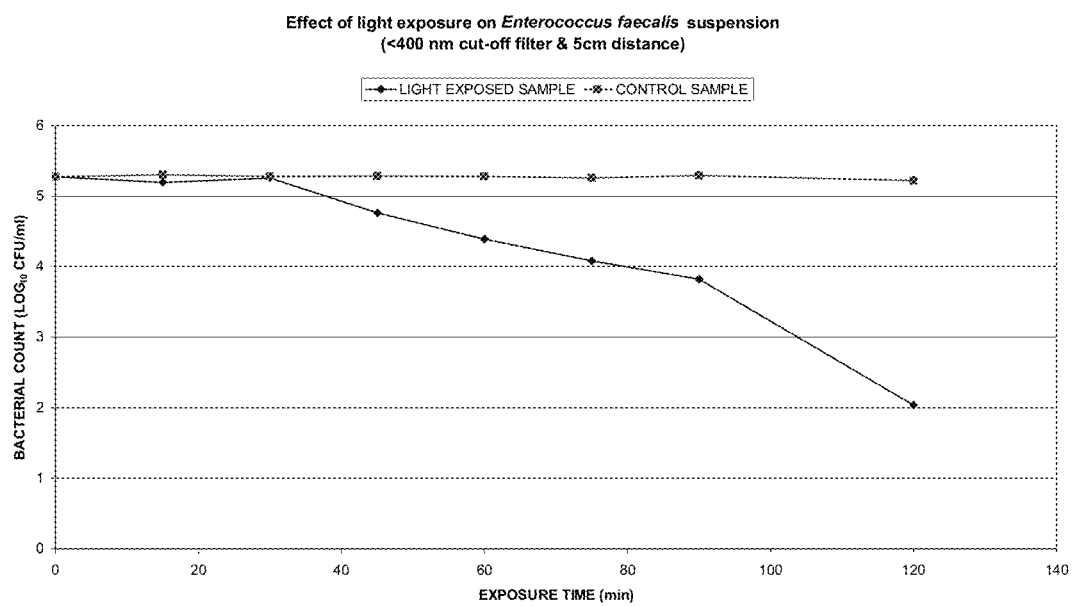
FIG. 8 is a plot of bacterial count of *Enterococcus faecalis* as a function of time of exposure to light of wavelength greater than 400 nm.

Suspensions of *Staphylococcus aureus* NCTC 4135 were also exposed to visible-light treatment. Again, the light beam was transmitted through a 400 nm long-wave pass filter before impacting on the bacterial suspension, allowing only the transmission of wavelengths of 400 nm and above. From FIG. 5 it can be seen that the Xenon light source caused significant reduction in the *Staphylococcus aureus* count even with a high starting bacterial population of approximately $10^7$ colony-forming units per milliliter (cfu/ml). Similar experiments were carried out using *Staphylococcus epidermidis* NCTC 7944, *Streptococcus pyogenes* NCTC 8198 and *Enterococcus faecalis*. The associated reductions in the bacterial population are shown in FIGS. 6, 7 and 8. In each of these a significant reduction in the bacterial count is observed.

Figure 9:
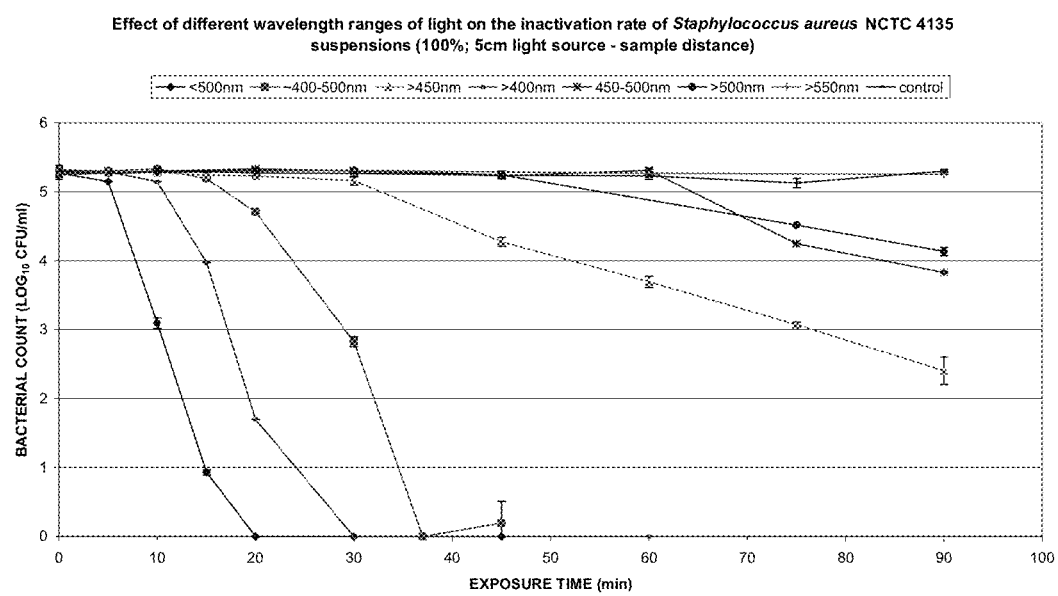
FIG. 9 is plots of bacterial count in a suspension of *S. aureus* NCTC 4135 as a function of time of exposure to light for different wavelength ranges.

Exposure tests using a range of filters were carried out. Bacterial suspensions were exposed to the following wavelength ranges for times up to 90 minutes: greater than 550 nm (using a 550 nm long-wave pass filter); greater than 500 nm (using a 500 nm long-wave pass filter), less than 500 nm (using a 500 nm short-wave pass filter); 400-500 nm (using a 400 nm long-wave pass filter and a 500 nm short-wave pass filter in combination); 450-500 nm (using a 450 nm long-wave pass filter and a 500 nm short-wave pass filter in combination); greater than 450 nm (using a 450 nm long-wave pass filter), and greater than 400 nm (using a 400 nm long-wave pass filter). The resultant inactivation curves in FIG. 9 allow only qualitative comparisons to be made since the filters do not have sharp cut-off wavelengths and the light intensities falling on the suspensions were different for the different curves. The results do however indicate that the wavelength region between 400 nm and 500 nm does provide a high rate of S. aureus inactivation.

Experiments were also carried out using bandpass filters each with a 10 nm FWHM (full-width, half-maximum). Suspensions of methicillin-resistant S. aureus LMG 15975 (approximately $10^5$ cfu/ml population) were exposed to visible light transmitted through the following bandpass filters: 400 nm, 405 nm, 410 nm, 415 nm, 420 nm, 430 nm, 440 nm, and 450 nm. The intensity of the lamp was altered for each filter to ensure that the light power at the suspension was the same for each measurement, thus allowing direct comparison of results. The results of these experiments showed that samples exposed using the 400 nm, 405 nm and 415 nm bandpass filters have a reduced colony-forming-unit count/ml; that is, light of wavelengths within these narrow bandwidths had an inactivating effect on the S. aureus strains.

Figure 10:
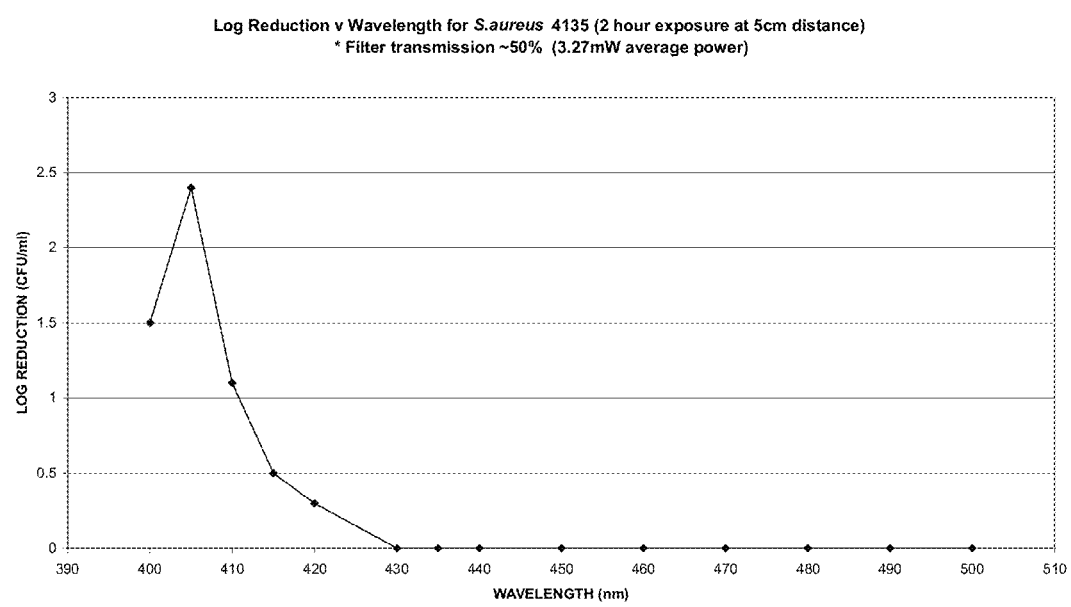
FIG. 10 is a plot of bacterial log reduction as a function of wavelength (400-500 nm) for *S. aureus* NCTC 4135.

A more detailed analysis of wavelength sensitivity was performed using suspensions of S. aureus NCTC 4135, and this is shown in FIG. 10. The results show that samples exposed using the 400 nm, 405 nm, 410 nm, 415 nm and 420 nm bandpass filters have a reduced colony-forming-unit count/ml; that is, light of wavelengths within these narrow bandwidths had an inactivating effect on the S. aureus strains. From these results it can be deduced that visible-light exposure over the wavelength range 400-450 nm is the major inducing factor for Staphylococcal inactivation, with increased inactivation occurring over the range 400-420 nm and optimum inactivation occurring at 405 nm. Moreover, it has been observed that a lower dose is required at this wavelength and typically the dose is less than 200 J/cm$^2$, such as less than 100 J/cm$^2$.

Figure 11:
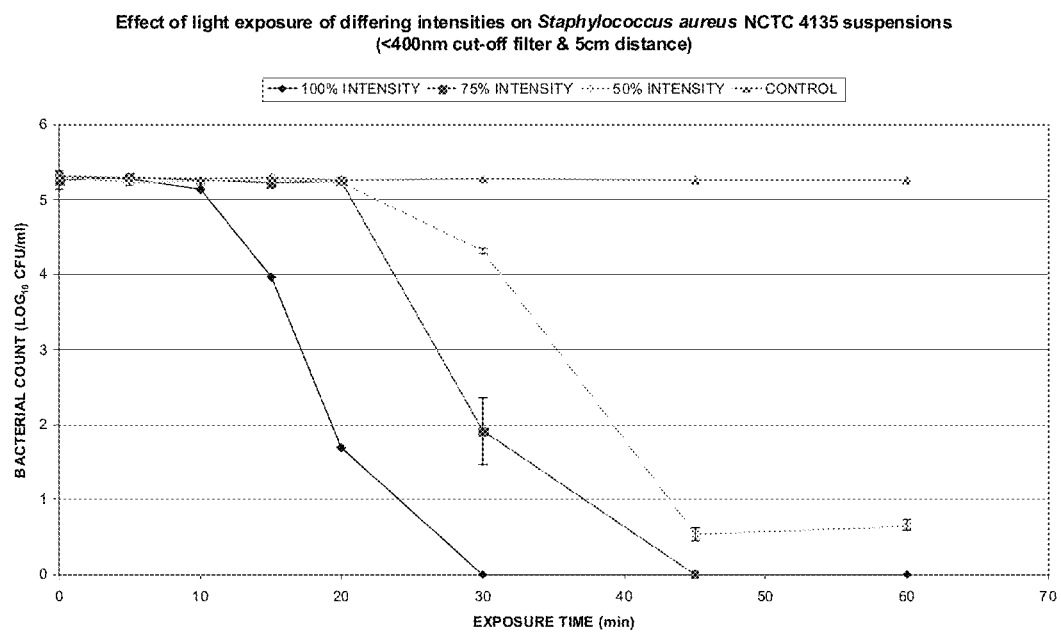
FIG. 11 is plots of bacterial count in a suspension of *S. aureus* NCTC 4135 as a function of time of exposure to light of wavelength greater than 400 nm for different light intensities.

In further experiments, Staphylococcus aureus NCTC 4135 suspensions were exposed to different intensities of visible-light treatment. These measurements were made using the 400 nm long-wave pass filter, that is, for wavelengths greater than 400 nm. FIG. 11 shows the results of these experiments. It can be seen that as the intensity of the light decreases, so to does the inactivation rate. The specific doses required for complete inactivation of Staphylococcal, Streptococcal and Enterococcal species using different filters and light intensities were determined. Sample results are shown in the Table below:

| ORGANISM | WAVELENGTH RANGE | DOSE (J/cm$^2$) | J/cm$^2$/log reduction |
| --- | --- | --- | --- |
| S. aureus 4135 | >400 nm (100% intensity) | 630 | 126 |
| S. aureus 4135 | >400 nm (75% intensity) | 729 | 145.8 |
| S. aureus 4135 | >400 nm (50% intensity) | 648 | 144 |
| S. aureus 4135 | <500 nm | 189.6 | 37.92 |
| S. aureus 4135 | 400-500 nm | 290.8 | 58.2 |
| MRSA 15975 | >400 nm | 1260 | 252 |
| MRSA 16a | >400 nm | 945 | 189 |
| S. epidermidis NCTC 7944 | >400 nm | 840 | 168 |
| Strep. pyogenes NCTC 8198 | >400 nm | 1440 | 288 |
| E. faecalis | >400 nm | 2880 | 1440 |

Figure 12:
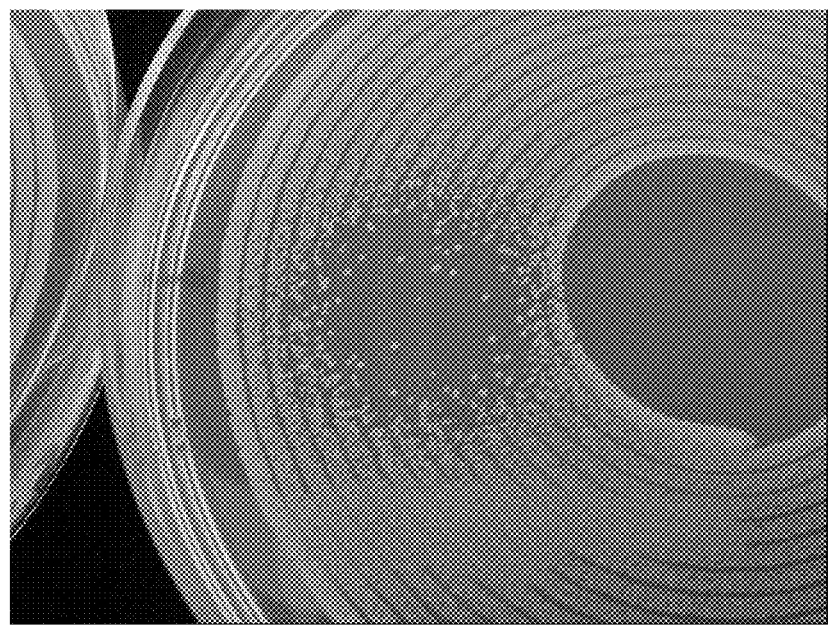
FIG. 12 is a visual indication of the surface inactivation of *S. aureus* NCTC 4135 through exposure to light of wavelengths greater than 400 nm. Surface inactivation is evidenced by inhibition of *S. aureus* growth on the areas exposed to this light.
Figure 13:
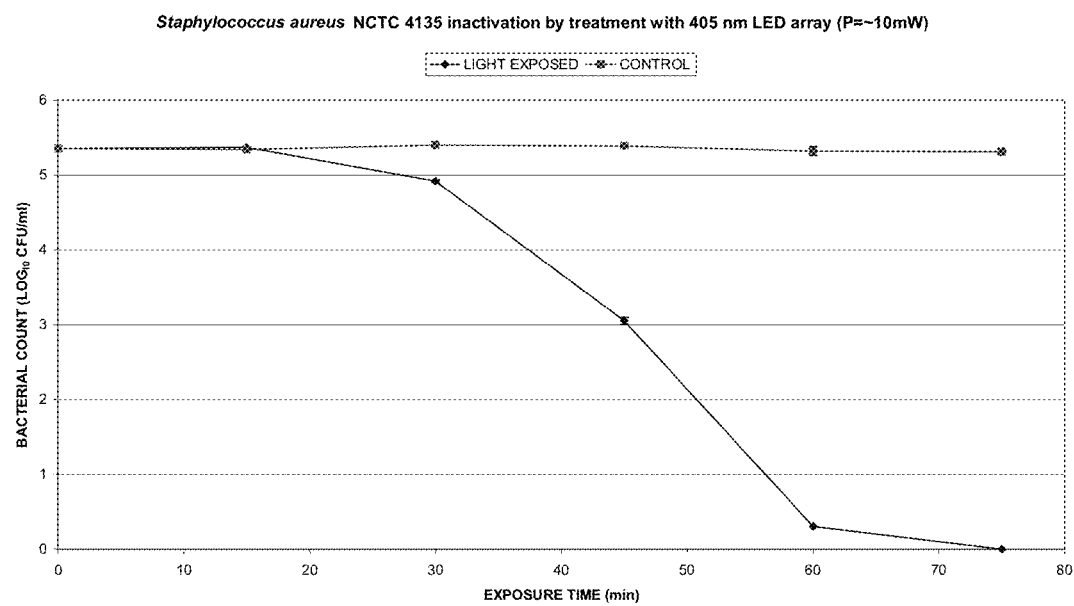
FIG. 13 is a plot of bacterial count of *S. aureus* NCTC 4135 as a function of time of exposure to light of 405 nm.
Figure 14:
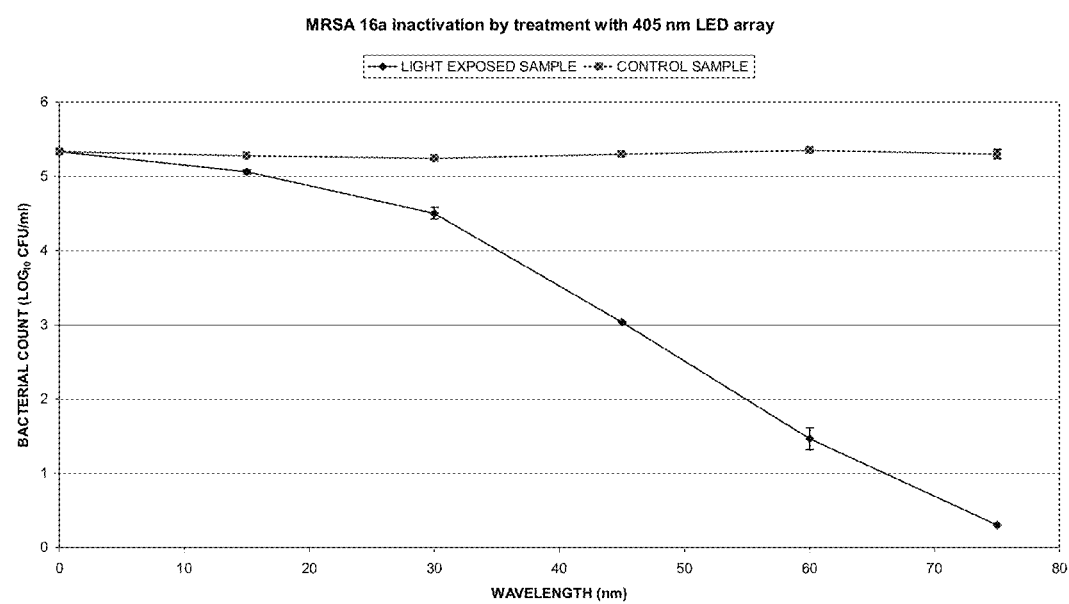
FIG. 14 is a plot of bacterial count of a methicillin-resistant *S. aureus* strain as a function of time of exposure to light of 405 nm.
Figure 15:
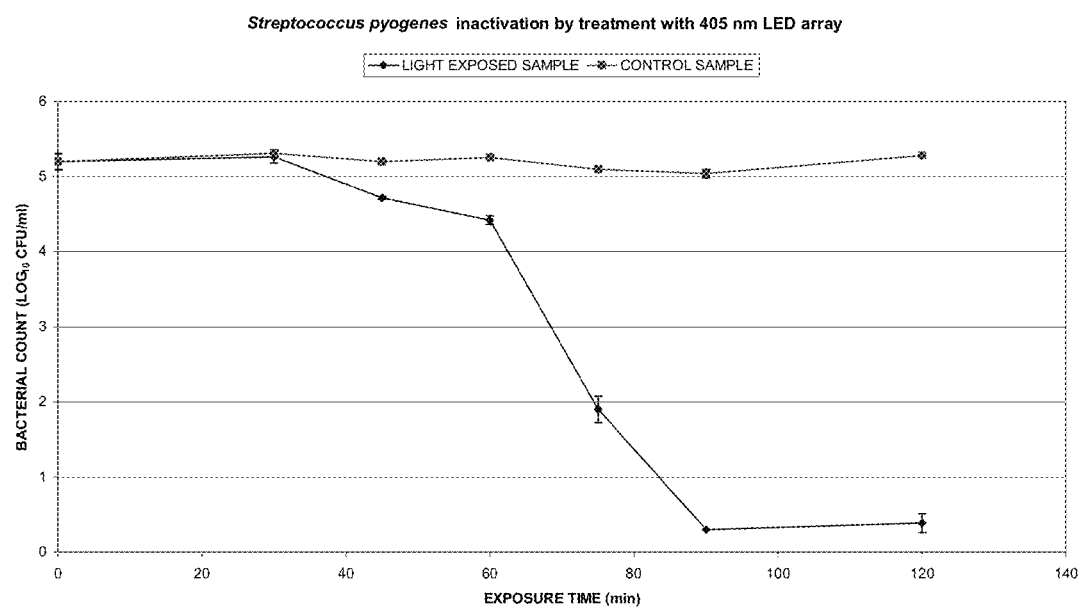
FIG. 15 is a plot of bacterial count of *Streptococcus pyogenes* NCTC 8198 as a function of time of exposure to light of 405 nm.
Figure 16:
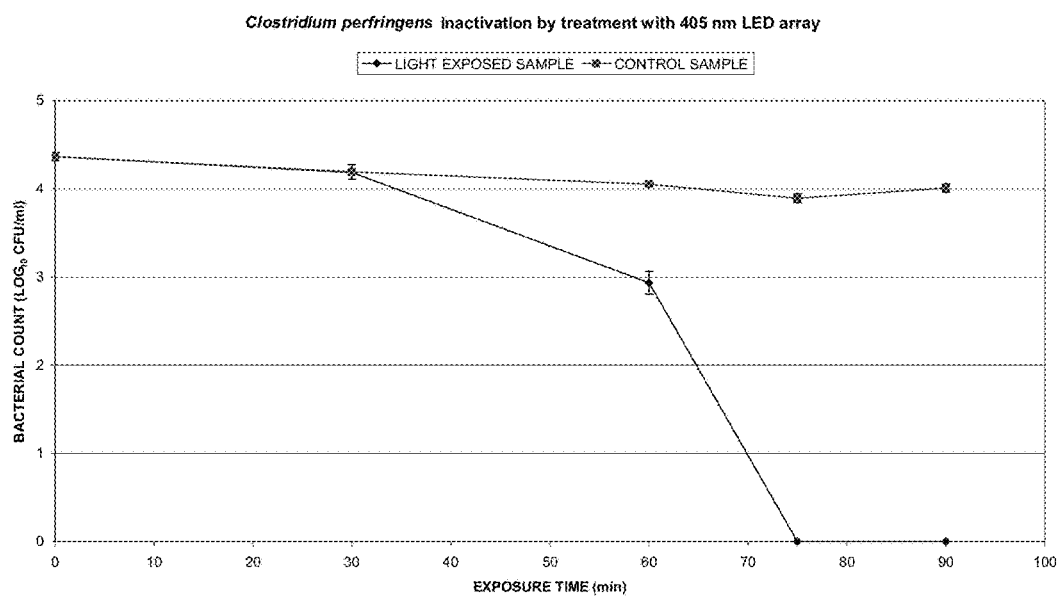
FIG. 16 is a plot of bacterial count of *Clostridium perfringens* 13124 as a function of time of exposure to light of 405 nm.

The effect of visible-light exposure for surface decontamination was also examined. This was done by exposing S. aureus cells, which were plated onto nutrient agar, to the light treatment (through a 400 nm long-wave pass filter) prior to incubation. Examples of results are shown as the areas of growth inhibition on the culture plates in FIG. 12.

A similar treatment system to that used with the Xenon lamp was assembled using a 405 nm LED array as a light source. Experiments were carried out using Staphylococcus aureus NCTC 4135, MRSA 16a, Streptococcus pyogenes NCTC 8198 and Clostridium perfringens 13124. The associated reductions in the bacterial population are shown in FIGS. 13, 14, 15 and 16, respectively. The specific doses required for complete inactivation of Staphylococcus, Streptococcus and Clostridium species using the 405 nm LED array were determined. Sample results are shown in the Table below:

| ORGANISM | WAVELENGTH | DOSE (J/cm$^2$) | J/cm$^2$/log reduction |
| --- | --- | --- | --- |
| S. aureus 4135 | 405 nm | 36 | 7.2 |
| MRSA 16a | 405 nm | 45 | 9 |
| Streptococcus pyogenes NCTC 8198 | 405 nm | 54 | 10.8 |
| Clostridium perfringens 13124 | 405 nm | 45 | 10.2 |

A comparison of the doses required for bacterial inactivation (5-log reduction) using light of wavelengths greater than 400 nm from the Xenon lamp and a 405 nm LED array is shown in the Table below:

| ORGANISM | DOSE (J/cm$^2$) | | J/cm$^2$/log reduction | |
| --- | --- | --- | --- | --- |
| | >400 nm | 405 nm | >400 nm | 405 nm |
| S. aureus NCTC 4135 | 630 | 36 | 126 | 7.2 |
| MRSA 16a | 945 | 45 | 189 | 9 |
| Cl. perfringens 13124 | 1440 | 54 | 288 | 10.8 |

The use of 400-500 nm, in particular 400-450 nm, wavelengths of visible light (blue light) has proved to be an effective means of inactivation of Staphylococcus strains, including MRSA, as well as CONS, Streptococcus, Enterococcus and Clostridium, with increased inhibition rates in the 400-420 nm range and in particular, around 405 nm. This demonstrates that a light source (continuous source, flashlamp, laser etc.) with output at wavelengths in these regions could potentially be used in clinical environments for the reduction in levels of methicillin-resistant Staphylococcus aureus, and other medically important Gram-positive species present in the air and on contact surfaces and materials, and most importantly, could be used for wound protection and tissue treatment. The exact parameters required would depend on the bacterial strain, the wavelength of the light being used and the light intensity. These can be readily determined experimentally.

Variations of the disclosed arrangements are possible without departing from the invention. For example, although both a Xenon lamp with a variety of different filters and a 405 nm LED array have been used as the inactivation source, it will be appreciated that any suitable light source can be used. Equally, although a particular experimental arrangement has been described here, it will be readily apparent that the light source used could be included in, for example, a hand-held device or could be designed to operate in or around areas that have to be kept free of MRSA. Accordingly the above description of the specific embodiment is made by way of example only and not for the purposes of limitation. It is clear that minor modifications may be made without significant changes to the operation described.

The invention claimed is:

1. A method for disinfecting air, contact surfaces or materials by inactivating one or more pathogenic Gram-positive bacteria in the air, on the contact surfaces or on the materials, said method comprising exposing the one or more pathogenic Gram-positive bacteria to visible light without using a photosensitizer, wherein the one or more pathogenic Gram-positive bacteria are selected from the group consisting of Methicillin-resistant *Staphylococcus aureus* (MRSA), Coagulase-Negative *Staphylococcus* (CONS), *Streptococcus, Enterococcus*, and *Clostridium* species, and wherein a portion of the visible light that inactivates the one or more pathogenic Gram-positive bacteria consists of wavelengths in the range 400-420 nm, and wherein the method is performed outside of the human body and the contact surfaces or the materials are non-living.

2. The method according to claim 1 wherein the visible light that inactivates has a wavelength of 405 nm.

3. A system for disinfecting air, contact surfaces or materials by inactivating one or more pathogenic Gram-positive bacteria in the air, on the contact surfaces or on the materials, the system comprising means for exposing said bacteria to visible light without using a photosensitizer, wherein the one or more pathogenic Gram-positive bacteria are selected from the group consisting of Methicillin-resistant *Staphylococcus aureus* (MRSA), Coagulase-Negative *Staphylococcus* (CONS), *Streptococcus, Enterococcus* and *Clostridium* species, and wherein a portion of the visible light that inactivates the one or more pathogenic Gram-positive bacteria consists of wavelengths in the range 400-420 nm, and wherein the system is for use outside of the human body and the contact surfaces or the materials are non-living.

4. The system according to claim 3 wherein the portion of the visible light that inactivates has a wavelength of 405 nm.

* * * * *

(12) INTER PARTES REVIEW CERTIFICATE (2812th)
United States Patent
Anderson et al.

(10) Number: US 9,839,706 K1
(45) Certificate Issued: Aug. 18, 2022

(54) INACTIVATION OF GRAM-POSITIVE BACTERIA

(71) Applicants: John Galloway Anderson; Michelle Maclean; Gerald Alexander Woolsey; Scott John MacGregor

(72) Inventors: John Galloway Anderson; Michelle Maclean; Gerald Alexander Woolsey; Scott John MacGregor

(73) Assignee: UNIVERSITY OF STRATHCLYDE

Trial Number:

IPR2019-00431 filed Dec. 12, 2018

Inter Partes Review Certificate for:

Patent No.: 9,839,706
Issued: Dec. 12, 2017
Appl. No.: 14/657,398
Filed: Mar. 13, 2015

The results of IPR2019-00431 are reflected in this inter partes review certificate under 35 U.S.C. 318(b).

INTER PARTES REVIEW CERTIFICATE
U.S. Patent 9,839,706 K1
Trial No. IPR2019-00431
Certificate Issued Aug. 18, 2022

AS A RESULT OF THE INTER PARTES REVIEW PROCEEDING, IT HAS BEEN DETERMINED THAT:

Claims 1-4 are found patentable.

\* \* \* \* \*